(12) United States Patent
Herbstreit et al.

(10) Patent No.: US 6,626,313 B2
(45) Date of Patent: Sep. 30, 2003

(54) CONTAINER FOR DELIVERY OF ICHNEUMON FLIES AND METHOD OF AGRICULTURAL PEST CONTROL USING SAME

(75) Inventors: Rolf Herbstreit, Waldachtal (DE); Bernd Wuehrer, Pfungstadt (DE)

(73) Assignees: fischerwerke Artur Fischer GmbH & Co. KG, Waldachtal (DE); AMW Nuetzlinge GmbH, Pfungstadt (DE)

( * ) Notice: Subject to any disclaimer, the term of this patent is extended or adjusted under 35 U.S.C. 154(b) by 0 days.

(21) Appl. No.: 09/876,591

(22) Filed: Jun. 7, 2001

(65) Prior Publication Data

US 2002/0008105 A1 Jan. 24, 2002

(30) Foreign Application Priority Data

Jun. 7, 2000 (DE) ......................... 100 27 767

(51) Int. Cl.⁷ ................................. B65D 8/18
(52) U.S. Cl. ............... 220/4.25; 220/789; 220/DIG. 30
(58) Field of Search ................... 220/4.25, DIG. 30, 220/787, 789; 43/132.1

(56) References Cited

U.S. PATENT DOCUMENTS

| | | | | |
|---|---|---|---|---|
| 1,764,039 A | * | 6/1930 | Cooper | 220/4.25 |
| 3,292,840 A | * | 12/1966 | Schmidt | 220/4.25 |
| 3,921,333 A | * | 11/1975 | Clendinning et al. | 47/74 |
| 3,932,319 A | * | 1/1976 | Clendinning et al. | 47/74 |
| 4,021,388 A | * | 5/1977 | Griffin | 523/128 |
| 5,248,035 A | * | 9/1993 | Gallagher | 206/427 |
| 5,792,496 A | * | 8/1998 | Fekete et al. | 220/4.21 |

FOREIGN PATENT DOCUMENTS

| | | | |
|---|---|---|---|
| DE | 2321800 | * | 11/1973 |
| DE | 38 22 931 C1 | | 1/1989 |
| DE | 298 07 847 U1 | | 10/1998 |
| FR | 1371240 | * | 7/1964 |
| FR | 2611732 A | * | 9/1988 |
| GB | 988970 | * | 4/1965 |

OTHER PUBLICATIONS

Standard Specification for Compostable Plastics, Designation: D 6400–99, in ASTM International, West Conshohocken, PA, United States, pp. 1–3.
"Process Economics Program Report 115", Published Aug., 1977, in.
Pruefung Der Kompostierbarkeit Von Kunststoffen, Teil 1: Chemische Pruefung, Din V 54900–1, Oct. 1998, pp. 1–15.
Die NTV Und Der Pflanzenschutz, in Gaertnerboese 03/99, p. 30.
Hassan, S., et al: "Massenzucht Und Anwendung Von Trichogramma ... ", in Gesunde Pflanzen, 42. JG., H. 11, 1990, pp. 387–394, p. 389.
Aid, Biologische Schaedlingsbekaempfung, 1990, p. 21.
Dega, H. 40, 1999, Anzeige Der Fa, Biobert, p. 37.

* cited by examiner

Primary Examiner—Stephen Castellano
(74) Attorney, Agent, or Firm—Michael J. Striker

(57) ABSTRACT

The container for delivery of ichneumon flies consists of ichneumon fly eggs and two biodegradable plastic parts (2,3) that are interlocked with one another. The ichneumon fly eggs are stuck on an inner wall (19) of the container. The container (1) is provided with at least one emergence opening (13), preferably a slit, of sufficient size for emergence of the hatched ichneumon flies. This container is rigid and enables automatic filling and delivery of the ichneumon flies by dropping the containers from a magazine, for example using small airplanes or model airplanes. The container decomposes after the container has been ploughed into the ground. A method of agricultural pest control using the containers is also part of the invention.

4 Claims, 1 Drawing Sheet

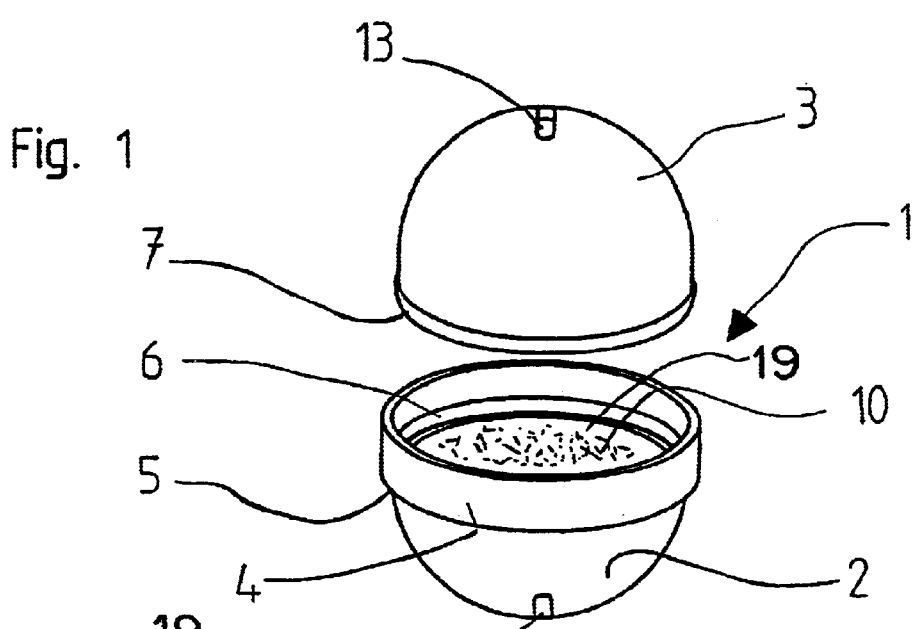
Fig. 1
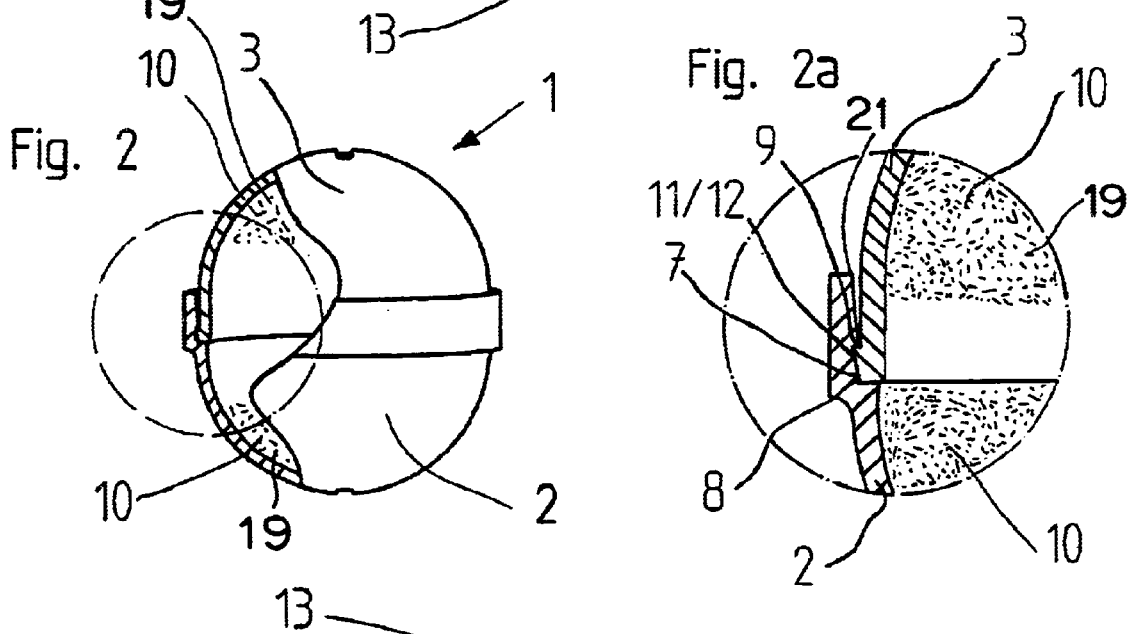
Fig. 2
Fig. 2a
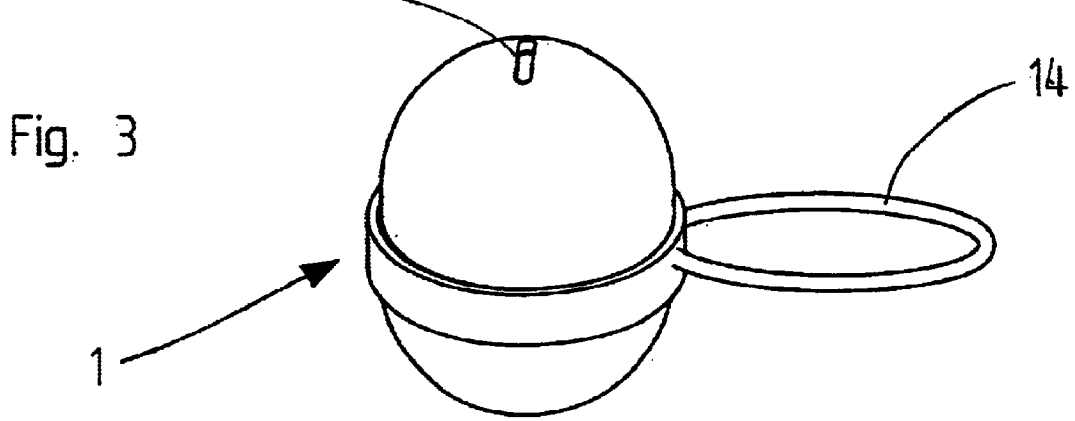
Fig. 3

CONTAINER FOR DELIVERY OF ICHNEUMON FLIES AND METHOD OF AGRICULTURAL PEST CONTROL USING SAME

BACKGROUND OF THE INVENTION

1. Field of the Invention

The present invention relates to a container for delivery of useful organisms, especially ichneumon flies, and to a method of agricultural pest control using a plurality of the containers.

2. Related Art

Ichneumon flies (Trichogramma) are used for biological pest control. The egg parasites of ichneumon flies are the natural enemies of many pests in agriculture and in vegetable and fruit cultivation. The ichneumon flies lay their own eggs in the eggs of the pests. They kill the pests and grow, inside the eggs, to the fully developed insect ready for flight. Adult ichneumon flies feed exclusively on pollen and honeydew. Naturally occurring populations are not sufficient for successful control. Ichneumon flies are therefore mass-multiplied and mass-delivered.

For their delivery, the ichneumon fly eggs are stuck onto a card support (Trichogramma card), which is suspended from the plant to be protected. Where the pest control is to be effected over a large surface area, for example in corn fields, a large number of Trichogramma cards have to be put out, which is done by hand with corresponding use of manpower.

SUMMARY OF THE INVENTION

It is an object of the present invention to provide a stable and residue-free decomposable container for the delivery of useful organisms, especially ichneumon flies, which container enables automatic filling and delivery from a magazine, for example using small airplanes.

According to the invention the container for the delivery of the useful organisms, especially ichneumon flies, is made of biodegradable material and consists of two parts that are connectable with each other and which has at least one emergence opening.

The two parts of the container, which are made from a biodegradable plastics material and are preferably hemispherical, are filled separately in an automatic filling system with approximately 1000 ichneumon fly eggs each, and the fly eggs are furthermore stuck to the inner wall of the hemispheres. The two hemispheres are then placed one on top of the other and connected to one another, for example using a clip connection. The manufacture of the container from a biodegradable plastics material using an injection-molding method and the dish shape, especially spherical shape, of the container provide rigidity, which allows the container to be introduced into a magazine and to be dropped from a relatively great height (for example for delivery using a small airplane or model airplane) without destroying the container.

A few days after delivery, the ichneumon flies hatch out and leave the container through the emergence openings. As a result of the deposition of their eggs in the eggs of the pests, the pests are killed. The next generation then emerges from the eggs of the ichneumon flies and continues the population process to protect the plants. The empty container made from biodegradable plastics material decomposes in the ground leaving no residue, especially after being ploughed in.

In order to be able to place the hemispheres upright, so that they do not tip over, on a work support for the automatic filling process, it is advantageous to provide the hemispheres with a circumferential collar at their outer rim.

It is also advantageous to make the emergence openings in the form of slits in order on the one hand to obtain a sufficiently large opening for emergence and on the other hand to prevent dirt from penetrating and blocking the openings.

Finally, in a further embodiment of the invention the container can be provided with a suspension device, which enables the containers also to be hung out individually on bushes or trees.

BRIEF DESCRIPTION OF THE DRAWING

The invention will be explained hereinafter in greater detail with reference to embodiments shown in the drawings, in which:

FIG. 1 is an exploded perspective view of a two-part container for useful organisms according to the invention in the open state;

FIG. 2 is a partially cutaway plan view of the two-part container shown in FIG. 1 in the closed state;

FIG. 2a is a sectional view of a part of the two-part container shown in the dashed circle in FIG. 2; and FIG. 3 is a perspective view of the container of FIG. 1 in the closed state with a suspension device.

DETAILED DESCRIPTION OF THE INVENTION

The container 1 consists of two dish-shaped hemispherical parts 2, 3, which are manufactured from biodegradable plastics using an injection-molding method. At the zenith of each of the two parts 2, 3, a slit-shaped emergence opening 13 is provided, the dimensions of which are approximately 0.5×5 mm. One part 2 has a circumferential collar 4 at its outer rim, which collar forms a bearing surface 5, 6 on both the inner wall and the outer wall of the part. By means of the outer bearing surface 5, the part 2 can be inserted, so that it does not tip over, into a seat in a work support of a device and can be conveyed to the filling station of a device (not shown). The inner stop surface 6 is used for positioning the other part 3 thereon, which part 3 also has a circumferential collar 7 that fits into the inner bore of the collar 4 of the part 2. In order to facilitate insertion of the part 3 into the part 2, the collar 7 of the part 3 has a shoulder surface 8. The collar 7 of the part 3 also has an outer bearing surface 9, which enables the part 3 to be placed upright in the seat of the work support without tipping over.

After the parts 2,3 have been filled with the ichneumon fly eggs 10 and after the eggs have been stuck to the inner wall 19 of the parts, the two parts 2,3 are fitted together and connected to one another by adhesion, jamming together or, as shown in the figures, by clipping. As catch means the part 2 has a circumferential groove 11 on the inner wall 21 of the collar 4, and the part 3 has projections 12 arranged on the collar 7, which engage in the groove 11.

Interlocking yields a spherical closed container 1 that has high rigidity to be obtained for storage in a magazine and for being dropped, without being destroyed, for large-surface-area delivery from a small airplane or model airplane. The individual containers stored in a magazine are used predominantly for biological pest control of relatively large surface areas, for example on cornfields. For pest control on trees, bushes or the like, according to the embodiment according to FIG. 3 the container 1 can be provided with a suspension device 14 which enables the containers of the invention to be hung individually. For more intensive pest control, it is possible to connect a plurality of containers together, for example in honeycomb formation.

The disclosure in German Patent Application 100 27 767.5 of Jun. 7, 2000 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in a container for delivery of useful organisms, especially ichneumon flies, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A method of delivering ichneumon flies over an extended surface area for agricultural pest control, wherein said method comprises the steps of:
   a) providing a number of containers, each of said containers consisting of a plurality of ichneumon fly eggs and two biodegradable plastic parts (2, 3), said two biodegradable plastic parts (2,3) having inner walls (19) with said ichneumon fly eggs (10) adhering to said inner walls, and wherein said two biodegradable plastic parts (2,3) are connected with each other to form a closed container for the ichneumon fly eggs, except that at least one of said two biodegradable plastic parts (2,3) is provided with at least one emergence opening (13) that is sufficiently large enough so that said ichneumon flies hatching from said ichneumon fly eggs leave through said at least one emergence opening;
   b) dropping said containers over the extended surface area without destroying said containers; and
   c) leaving said containers on the extended surface area for a time sufficient for hatching of said ichneumon fly eggs and emergence of the ichneumon flies from said containers;
   whereby said ichneumon flies kill agricultural pests by deposition of further ichneumon fly eggs in eggs of said pests and said containers decompose leaving no residue.

2. The method as defined in claim 1, wherein at least about 2000 of said ichneumon fly eggs adhere to said inner walls of said biodegradable plastic parts of each of said containers.

3. The method as defined in claim 1, wherein said biodegradable plastic parts (2,3) of each of said containers are each hemispherical, have respective outer rims and are formed to interlock with each other so that the container has rigidity sufficient to withstand being dropped.

4. The container as defined in claim 1, wherein said at least one emergence opening consists of a slit provided in one of said two biodegradable plastic parts of each of said containers.

\* \* \* \* \*